United States Patent
Smith et al.

(10) Patent No.: US 10,274,402 B2
(45) Date of Patent: Apr. 30, 2019

(54) BIOLOGICAL SAMPLE MATERIAL COLLECTION

(71) Applicant: GE Healthcare UK Limited, Buckinghamshire (GB)

(72) Inventors: Michael John Smith, Cardiff South Glamorgan (GB); Peter James Tatnell, Cardiff South Glamorgan (GB); Leonard Goren, San Francisco, CA (US)

(73) Assignee: GE Healthcare UK Limited, Little Chalfont (GB)

( * ) Notice: Subject to any disclaimer, the term of this patent is extended or adjusted under 35 U.S.C. 154(b) by 405 days.

(21) Appl. No.: 14/913,248

(22) PCT Filed: Aug. 7, 2014

(86) PCT No.: PCT/EP2014/066980
§ 371 (c)(1),
(2) Date: Feb. 19, 2016

(87) PCT Pub. No.: WO2015/028274
PCT Pub. Date: Mar. 5, 2015

(65) Prior Publication Data
US 2016/0202151 A1    Jul. 14, 2016

(30) Foreign Application Priority Data
Aug. 30, 2013   (GB) .................... 1315522.1

(51) Int. Cl.
*B01L 3/00*      (2006.01)
*G01N 1/10*      (2006.01)
*B29C 44/02*     (2006.01)
*B29C 44/10*     (2006.01)
*A61F 13/38*     (2006.01)
(Continued)

(52) U.S. Cl.
CPC ............... *G01N 1/10* (2013.01); *A61F 13/38* (2013.01); *A61F 13/385* (2013.01); *B29C 44/025* (2013.01); *B29C 44/10* (2013.01); *A61F 2013/530007* (2013.01); *B29K 2105/04* (2013.01); *B29K 2105/16* (2013.01);
(Continued)

(58) Field of Classification Search
None
See application file for complete search history.

(56) References Cited

U.S. PATENT DOCUMENTS

2007/0249961 A1* 10/2007 Morrison ........... A61B 10/0045
                                                    600/572
2010/0106057 A1  4/2010 Harvey et al.
2014/0289986 A1* 10/2014 Hani ..................... A61F 13/38
                                                    15/209.1

FOREIGN PATENT DOCUMENTS

CN        202351074 U    7/2012
CN        202752252 U    2/2013
WO    WO-2013113842 A1 * 8/2013  ............... G01N 1/02

OTHER PUBLICATIONS

International Search Report and Written Opinion regarding International Application No. PCT/EP2014/066980, dated Nov. 6, 2014, 8 pages.

* cited by examiner

Primary Examiner — Dennis White
(74) Attorney, Agent, or Firm — Eversheds Sutherland (US) LLP

(57) ABSTRACT

A biological sample collection device 10 is disclosed including a shaped sample collecting tip 20a, said tip at least being formed from a fibrous material mixed with a liquid to form a pulp, said pulp being solidified to form the shape of the tip.

12 Claims, 2 Drawing Sheets

(51) Int. Cl.
*B29K 105/04* (2006.01)
*B29K 105/16* (2006.01)
*B29K 511/00* (2006.01)
*B29L 31/00* (2006.01)
*A61F 13/53* (2006.01)

(52) U.S. Cl.
CPC ..... *B29K 2511/00* (2013.01); *B29L 2031/772* (2013.01); *G01N 2001/1056* (2013.01)

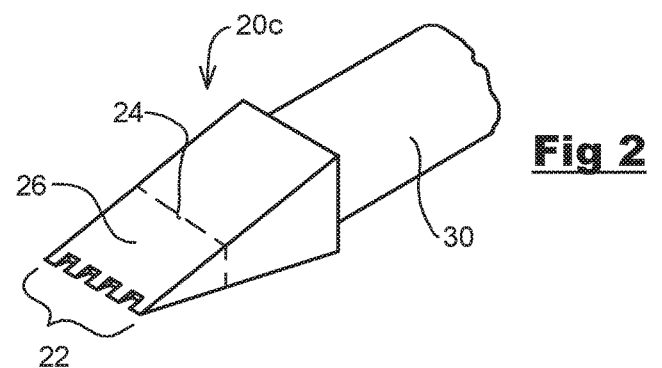
Fig 2
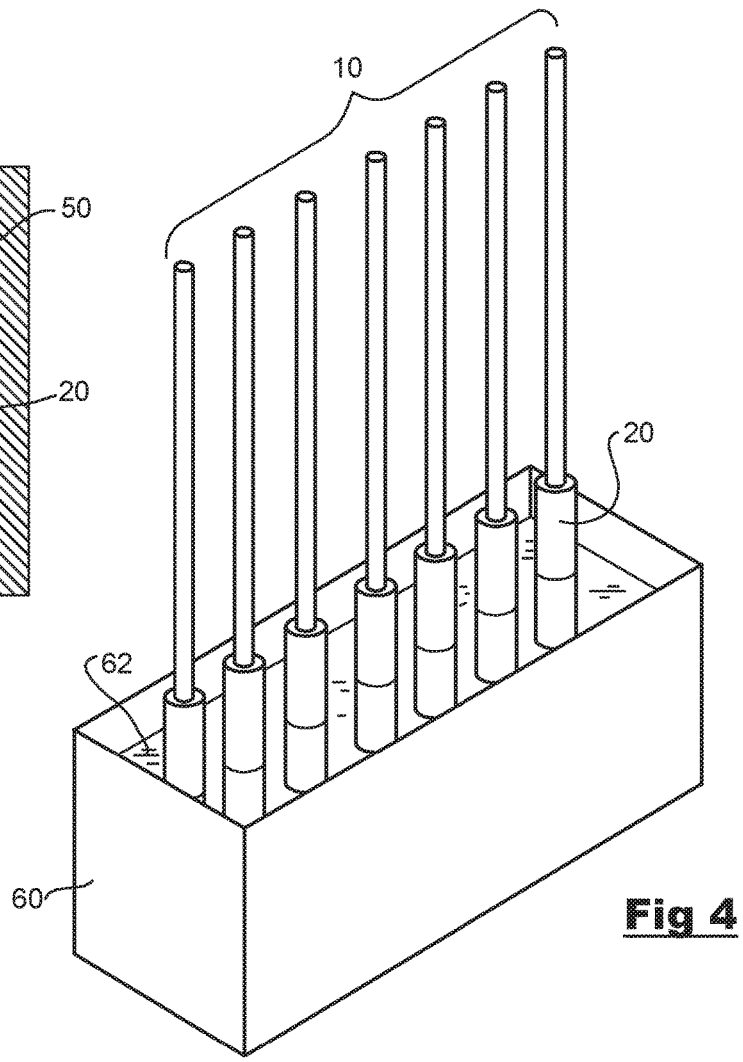
Fig 3
Fig 4

BIOLOGICAL SAMPLE MATERIAL COLLECTION

CROSS REFERENCE TO RELATED APPLICATION

This application is a filing under 35 U.S.C. 371 of international application number PCT/EP2014/066980, filed Aug. 7, 2014, which claims priority to Great Britain application number 1315522.1, filed Aug. 30, 2013, the entire disclosures of each of which are hereby incorporated by reference.

BACKGROUND

This invention relates to a collection device for collecting a biological sample, for example for clinical diagnosis, or at a crime scene, and a method for making the same.

Samples often found at crime scenes include blood, semen etc. Often the infectious content of these samples is unknown, for example, it is possible for blood derived from intravenous drug users to be contaminated with pathogenic viruses such as Hepatitis B. That particular virus is relatively stable and remains infectious for weeks even when exposed to typical ambient conditions. So it is important for the sample collector to avoid becoming infected with potentially harmful diseases. Similar concerns exist for the collection of samples for clinical diagnosis purposes e.g. during sample collection of potential sexual transmitted diseases.

In order to mitigate these concerns, protect gloves are worn, but these are regularly punctured particularly where sharp needles are handled. The inventors have realised that the device used for sample collecting is of great importance in reducing the risks of becoming infected. A rigid collection device allows easier use, for example for rubbing on a surface or forcing the device into a narrow area, which ease of use also affords more controlled handling and therefore safer use, with less risk of infection for the sample collector by slipping or forcing the collector in a manner which leads to infection or contamination.

It is also very important to avoid contaminating a patient when collecting a biological sample and to avoid contaminating a crime scene. Prior collection devices are adequate for their purpose, but are often difficult to use because their shape is often not ideal for their collection purpose. To date, known collection tools have been in the form of soft foam or sponge pads, paper sheets, cotton buds and the like, which are shaped as a compromise to suit a variety of needs and shapes based on the strength limitations of the material used. For example, cotton fibres are wound together to form a teardrop shaped bud on a support are popular because they can fit into many small spaces, and their shape has mechanical strength stability by virtue of their round bud formation. However, these buds cannot reach narrow cracks or similar small spaces. Other formations made from paper have been used to good effect. The drawback with these materials is that there is a limit as to what shape the collection portions can be, based on limitations in strength of the material used. Paper is generally flat, or could be folded to add a little extra strength. Soft foamed polymer material can be cut to any shape, but it has little inherent strength and so is seldom formed into an elongated tip. Since the foam is weak, it is difficult to force it into narrow spaces. Stronger foamed materials are available but these have reduced wicking ability which is important for collecting samples.

The inventors have realised that a sample collection device which has inherent strength, and yet will readily accept a biological sample is far simpler and safer to use and mitigates the risks of slipping or otherwise accidentally coming into contact with a surface or object from which the sample is taken.

An additional way to mitigate risks from pathogens is to chemically coat the sample collecting tip, but this is not possible with some materials, for example, foamed polymers do not readily accept chemical coatings, because they do not wick liquids readily.

SUMMARY

According to a first aspect of the invention, there is provided a biological sample collection device including a shaped sample collecting tip, said tip at least being formed from a fibrous material mixed with a liquid to form a pulp, said pulp being solidified to form the shape of the tip.

Preferably, the pulp is solidified by compression, for example in a mould.

Alternatively, the pulp is solidified by drying in an open mould.

Alternatively, the pulp is solidified by setting or curing, for example the liquid may be a settable porous or semi porous material such as gypsum.

In an embodiment, the fibrous material is cellulose fibres and the liquid is water.

In an embodiment, the fibrous material is glass fibres.

In an embodiment, the device further includes a hollow plastics handle portion.

In an embodiment, the handle is separable from the tip, for example by forcing the tip off the handle by means of a pusher incorporated into the handle. The advantage of this is that only the small sample collection area will need to be transported for subsequent examination. The plastics handle and pusher can then be disposed of.

Alternatively, the device further includes a handle portion formed also from said solidified pulp. In this instance there may be provided a plastics case for housing and transporting the device.

In an embodiment, the tip is shaped as a round, triangular, or other polygonal cylinder; or as a wedge.

In an embodiment, a chemical composition is applied to the pulp, (either before or after it is solidified).

Preferably said chemical composition is a solution, including:
 (i) a monovalent weak base (such as "Tris", tris-hydroxymethyl methane, either as the free base or as the carbonate);
 (ii) a chelating agent (such as EDTA, ethylene diamine tetracetic acid); and
 (iii) an anionic detergent (such as SDS, sodium dodecyl sulphate); and optionally
 (iv) uric acid or a urate salt.

This solution may be incorporated into or absorbed on the surface of the pulp, for example by mixing with the pulp prior to solidification, or by spraying the solution onto the solidified pulp, or dipping the solidified pulp into the solution.

This composition has the advantage that it also protects against degradation of DNA captured on the tip.

In an embodiment, the tip includes an area of relative weakness, for example, a perforated delineation, of sufficient weakness that parts of the tip can be separated manually. This feature will allow the conservation of a portion of the sample on the unseparated remainder of the tip, for storage and possible repeat testing.

The advantages of embodiments of the proposed device is that the use of pulped material will allow i) sample collection devices to be easily engineered into specific shapes to facilitate the direct collection of potentially infectious material from crime scenes etc., and ii) will significantly improve the ease of manufacturing.

According to a second aspect of the invention, there is provided a biological sample collection device including a sample collecting tip shaped substantially as illustrated in any one of the Figures, said tip at least preferably being formed from a fibrous material mixed with a liquid to form a pulp, said pulp being solidified to form the shape of the tip.

The invention extends to a method for producing a shaped collecting tip for a biological sample collector, including the following steps, in any suitable order:

a) providing a fibrous material mixed with a liquid to form a pulp; and
b) solidifying said pulp to form the shaped tip;

The solidify step may comprise, one or more of: compression, for example in a mould; drying; for example in an open mould; or setting or curing, for example the liquid may be a settable porous or semi porous material.

BRIEF DESCRIPTION OF THE DRAWINGS

The invention can be put into effect in numerous ways. By way of example, embodiments are described below, with examples being illustrated in the drawings.

FIG. 2 shows an enlarged view of the tip of the sample collector of FIG. 1c;

FIG. 3 shows a sectional view of the sample collector of FIG. 1a; and

FIG. 4 shows apparatus for coating the sample collectors shown in the preceding drawings.

DETAILED DESCRIPTION

Figure 1:
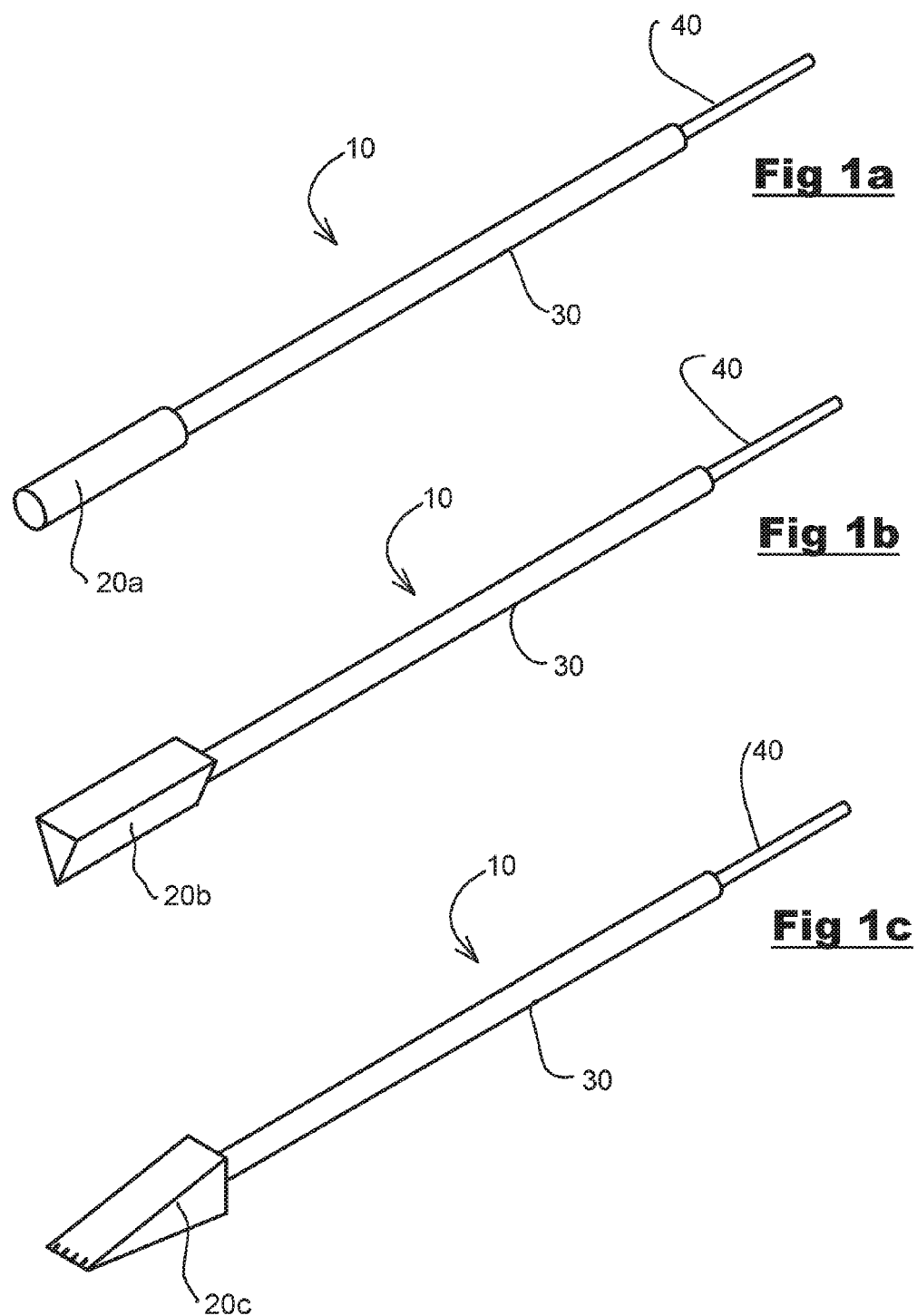
FIGS. 1a, 1b and 1c show perspective views of three alternative sample collectors.

Referring to FIG. 1a there is shown a sample collector 10 which includes a collecting tip 20a, described in more detail below, attached to a hollow elongate plastics handle 30 and an ejecting rod 40 which is slideable within the hollow handle 30. Similar collectors 10 are shown in FIGS. 1b and 1c, where like features are referenced with like numerals. Each sample collector differs by having a differently shaped collecting tip 20a, 20b or 20c.

Tips 20 are three dimensional and, in these embodiments: tip 20a is generally cylindrical; tip 20b is a triangular prism; and tip 20c is wedge shaped having its thin end pointing away from its respective handle 30. Referring additionally to FIG. 2 the tip 20c has pointed castellations 22 formed at its thin edge. This three dimensional shape adds significantly to the mechanical strength of the tips, and thereby their ease/ safety in use.

In use, the tips 20a, 20b and 20c are manipulated to absorb or otherwise collect a sample of biologic material, which can then be stored, and/or analysed, by known techniques. The castellations of tip 20c provide a better chance of collecting minute quantities of sample material, for example from a crime scene. The collecting action will involve gentle rubbing of the tip on a surface, or on the skin.

FIG. 3 shows a cross section through the ends of the sample collector 10. A cylindrical tip 20a is shown in FIG. 3, however, the same constructional principles apply to sample collectors which utilise tips of other shapes.

The tips are formed from a pulp of fibres and a liquid. Herein, the word pulp is used to describe a generally soft mass with very little inherent strength, akin to pulped paper. In this example, the fibres are cellulose fibres, of a grade commonly used for paper making, and the liquid is water. The pulp is placed on one half of a split mould 50, which mould has a cavity corresponding to the desired tip shape, and an opening 52 for accepting a handle 30, which is inserted into the mould cavity along with the pulp. The volume of pulp in the mould is sufficient that when the halves of the mould are compressed around the pulp, the pulp is compressed also and excess liquid is squeezed out from the join line of the mould halves. Thus the pulp is solidified around a portion of the handle 30. The tip and handle are then removed from the mould and allowed to dry, for example by heating which adds additional strength. The tip is releasably held on the handle 30, such that when the handle 30 is held and finger pressure is exerted on the pusher 40, the tip can be pushed off the handle, but will remain in place while sample collecting takes place.

Referring to FIG. 4, the solidified tips are conditioned with a chemical composition that is capable of carrying out several functions: (i) lyse intact cellular material upon contact, releasing genetic material, (ii) enable and allow for the conditions that facilitate genetic material immobilization to the tip (by a combination of mechanical and chaotrophic effects), (iii) maintain the immobilized genetic material in a stable state without damage due to degradation, endonuclease activity, UV interference, and microbial attack, (iv) maintain the genetic material as a support-bound molecule that is not removed from the tip during any downstream processing, and v) inhibit potentially infectious pathogenic activity as mentioned above.

The dried tips 20 are dipped in liquid bath 60 containing a solution 62 of a chemical composition, namely:

(v) a monovalent weak base in the form of tris-hydroxymethyl methane (Tris'), which may be a free base or as a carbonate);
(vi) a chelating agent in the form of ethylene diamine tetracetic acid (EDTA); and
(vii) an anionic detergent in the form of sodium dodecyl sulphate (SDS); and optionally
(viii) uric acid or a urate salt.

The dipped tips can then be dried again, ready for use.

It is only necessary to provide the tip surfaces with such a composition, and so a momentary dipping is all that is required. Such a momentary dipping should provide a dried surface having a treated layer having the approximate quantities per square centimeter as follows:

(i) EDTA: 0.5 micromols (146.1 mg of free acid)
(ii) Tris': 8 micromols (968.8 mg of free base)
(iii) SDS: 1 mg; and optionally
(iv) uric acid: 2 micromols (336.24 mg of acid).

An important characteristic of the tips described and illustrated is their water absorption ability or wicking. In part, this can be controlled by type and size of fibres used, and the degree of compression, which is used to compress those fibres. A high wicking ability is desired, but the higher the wicking ability, generally, the weaker the tip structure. A wicking ability of at least 1 or 2 grams of water per second of immersion in water at 26.666 degrees Celsius (80 degrees Fahrenheit) is considered to be adequate whilst providing sufficient mechanical tip strength. Higher wicking ability also affords quicker drying of the tip once a liquid sample has been collected on the tip, which is important if the tip is to be stored in a dry state.

Although three similar embodiments only have been illustrated, it will be apparent to the skilled addressee that modifications, variants, additions and omissions are possible within the scope and spirit of the invention defined herein.

For example, the tip shapes could be any three dimensional shape to suit their application. Since the shape can be moulded, the shape could be irregular.

Production of the tips has been described above as being moulded by compression, but other production techniques could be used. For example the tip could be solidified in an open mould, wherein the pulp can be air dried to form a shape. This reduces costs, which is particularly important for small batches and increases wicking. The pulp could also be mixed with a setting liquid, such as a porous resin, or cementitious composition, and allowed to set in a mould, for example an open mould. This adds significantly to the strength of the tip.

It is preferred that the tip 20 is moulded to the handle 30, but the tip may be affixed by means of adhesive or a mechanical fastening to provide increased holding strength. However, the ease with which the tip can be detached using the pusher 40 will be impaired, and so the pusher may be omitted in this alternative. To aid removal of a sample from a tip, as an alternative, the tip may have an area of weakness (24 FIG. 3) so that only an end 26 of the tip 20 is removed for subsequent analysis.

Although a plastics handle 30 is illustrated, that handle may be formed from the same material as the tip to simplify further the production of the sample collector. In such cases, there may be an area of weakness similar to the area 24, or the whole sample collector may be transported for subsequent analysis.

The tips illustrated are described as being made from cellulose fibres, but other fibres could be used, for example glass fibres.

Dipping of the tips into a chemical composition is described above, but other methods of applying the chemical composition could be employed. For example the composition could be incorporated into the pulp prior to its solidification, or it may be absorbed on the surface of the pulp, prior to solidification. The composition may also be sprayed in solution onto the solidified pulp, before or after drying.

What is claimed is:

1. A rigid biological sample collection device including a shaped sample collecting tip, said tip at least being formed from a fibrous material mixed with a liquid to form a pulp, said pulp being solidified to form the shaped tip having inherent strength for allowing rubbing of the tip on a surface for sample collection, wherein the device further includes a hollow plastic elongate handle portion, and an ejector rod slideable within the hollow handle, the handle, rod and tip forming said rigid collection device, and wherein the tip is releasably held to the handle such that the tip and handle are separable, by forcing the tip off the handle by movement of the rod in the handle and wherein the tip is chemically conditioned.

2. A device as claimed in claim 1, wherein the pulp is solidified by compression, optionally in a mould.

3. A device as claimed in claim 1, wherein the pulp is solidified by drying in an open mould.

4. A device as claimed in claim 1, wherein the pulp is solidified by setting or curing.

5. A device as claimed in claim 1, wherein the fibrous material is cellulose fibres and the liquid is water.

6. A device as claimed in claim 1, wherein the fibrous material is glass fibres.

7. A device as claimed in claim 1, wherein the handle portion is formed also from said solidified pulp.

8. A device as claimed in claim 1, wherein the tip is shaped as a round, triangular, or other polygonal cylinder; or as a wedge.

9. A device as claimed in claim 1, wherein a chemical composition is applied to the pulp for the chemical conditioning, either before or after it is solidified.

10. A device as claimed in claim 9, wherein said chemical composition is a solution, including:
    (i) a monovalent weak base (such as "Tris", tris-hydroxymethyl methane, either as the free base or as the carbonate);
    (ii) a chelating agent (such as EDTA, ethylene diamine tetracetic acid); and
    (iii) an anionic detergent (such as SDS, sodium dodecyl sulphate); and optionally
    (iv) uric acid or a urate salt.

11. A device as claimed in claim 10, wherein said solution is incorporated into or absorbed on the surface of the pulp, by mixing with the pulp prior to solidification, or by spraying the solution onto the solidified pulp, or dipping the solidified pulp into the solution.

12. A device as claimed in claim 1, wherein the tip includes an area of relative weakness, of sufficient weakness that parts of the tip can be separated manually.

* * * * *